United States Patent [19]
Tempkin et al.

[11] Patent Number: 5,811,544
[45] Date of Patent: Sep. 22, 1998

[54] PROCESS FOR PREPARING 1,4,8,11-TETRAAZACYCLOTETRADECANE

[75] Inventors: Orin Tempkin, Edison; Prasad Kapa, Parsippany, both of N.J.

[73] Assignee: Johnson Matthey PLC, London, England

[21] Appl. No.: 690,105

[22] Filed: Jul. 30, 1996

Related U.S. Application Data

[60] Provisional application No. 60/003,076 Aug. 28, 1995.
[51] Int. Cl.$^6$ .................................................. C07D 255/02
[52] U.S. Cl. ............................................ 540/470; 540/450
[58] Field of Search ...................................... 540/450, 470

[56] References Cited

U.S. PATENT DOCUMENTS 5,047,527  9/1991  Handel et al. ........................... 540/474
5,608,061  3/1997  Ciszewski et al. ...................... 540/470

OTHER PUBLICATIONS

Bradshaw et al; Chap IV in Azacrown Macrocycles; pp. 145–149, An Interscience Publication, John Wiley & Sons, Inc; 1993.

*Primary Examiner*—Mukund J. Shah
*Assistant Examiner*—Pavanaram K. Sripada
*Attorney, Agent, or Firm*—Pillsbury Madison & Sutro LLP

[57] ABSTRACT

An improved process for preparing 1,4,8,11-tetraazacyclotetradecane comprising the bisacylation of an acyclic diamine to obtain a dichlorodiamide compound in a first step, the cyclization of said diamide compound to obtain dioxocyclam in a second step, and the reduction of dioxocyclam in a third step to obtain the desired 1,4,8,11-tetraazacyclotetradecane.

11 Claims, No Drawings

PROCESS FOR PREPARING 1,4,8,11-TETRAAZACYCLOTETRADECANE

This application is based on provisional application No. 60/003,076, filed Aug. 28, 1995, the priority benefit thereof being claimed herein.

BACKGROUND OF THE INVENTION

1. Field of the Invention

The present invention relates to the area of cyclic tetraamines and, more particularly, relates to an improved process for preparing a specific cyclic tetraamine which is a valuable starting material in the preparation of a specific pharmaceutically active 1,4-phenylenebis(methylene)-linked cyclam dimer.

2. Description of the Prior Art

U.S. Pat. No. 5,021,409 is directed to a method of treating retroviral infections comprising administering to a mammal in need of such treatment a therapeutically effective amount of a bicyclic macrocyclic polyamine compound. Although the usefulness of certain alkylene and arylene bridged cyclam dimers is generically embraced by the teachings of the reference, no arylene bridged cyclam dimers are specifically disclosed. In addition, although no specific processes are set forth for preparing the alkylene and arylene bridged cyclam dimers, it is believed that at least some of them are prepared employing 1,4,8,11-tetraazacyclotetradecane (aka. cyclam) as the starting material.

WO 93/12096 discloses the usefulness of certain linked cyclic polyamines in combating HIV and pharmaceutical compositions useful therefor. Among the specifically disclosed compounds is 1,1'-[1,4-phenylenebis-(methylene)]-bis-1,4,8,11-tetraazacyclotetradecane (and its acid addition salts), which compound is a highly potent inhibitor of several strains of human immune deficiency virus type 1 (HIV-1) and type 2 (HIV-2). Although no specific processes are set forth for preparing said compound, it is believed to be prepared employing 1,4,8,11-tetraazacyclotetradecane as the starting material.

European Patent Appln. 374,929 discloses a process for preparing mono-N-alkylated polyazamacrocycles comprising reacting the unprotected macrocycle with an electrophile in a non-polar, relatively aprotic solvent in the absence of base. Although one of the specifically disclosed macrocycles is 1,4,8,11-tetraazacyclotetradecane, it is indicated to have been purchased commercially from Aldrich Chemical Co.

U.S. Pat. No. 5,047,527 is directed to a process for preparing a monofinctionalized (e.g., monoalkylated)cyclic tetraamine comprising: 1) reacting the unprotected macrocycle with chromium hexacarbonyl to obtain a triprotected tetraazacycloalkane compound; 2) reacting the free amine group of the triprotected compound prepared in 1) with an organic (e.g., alkyl) halide to obtain a triprotected monofinctionalized (e.g., monoalkylated) tetraazacycloalkane compound; and 3) de-protecting the compound prepared in 2) by simple air oxidation at acid pH to obtain the desired compound. In addition, the reference discloses alternative methods of triprotection employing boron and phosphorous derivatives and the preparation of linked compounds, including the cyclam dimer 1,1'-[1,4-phenylenebis-(methylene)]-bis-1,4,8,11-tetraazacyclotetradecane, by reacting triprotected cyclam prepared as set forth in 1) above with an organic dihalide in a molar ratio of 2:1, and deprotecting the resultant compound to obtain the desired cyclam dimer. Although one of the specifically disclosed macrocycles is cyclam, since no mention is made regarding its method of preparation, it is believed to have been obtained commercially.

J. Med. Chem., Vol. 38, No. 2, pgs. 366–378 (1995) is directed to the synthesis and anti-HIV activity of a series of novel phenylenebis(methylene)-linked bis-tetraazamacrocyclic analogs, including the known cyclam dimer 1,1'-[1,4-phenylenebis(methylene)]-bis-1,4,8,11-tetraazacyclotetradecane. The cyclam dimers disclosed in this reference, including the afore-mentioned cyclam dimer, are prepared by: 1) forming the tritosylate of the tetraazamacrocycle; 2) reacting the protected tetraazamacrocycle with an organic dihalide, e.g., dibromo-p-xylene, in acetonitrile in the presence of a base such as potassium carbonate; and 3) de-protecting the bis-tetraazamacrocycle prepared in 2) employing freshly prepared sodium amalgam, concentrated sulfuric acid or an acetic acid/hydrobromic acid mixture to obtain the desired cyclam dimer, or an acid addition salt thereof. Although one of the specifically disclosed macrocycles is cyclam, it is indicated to have been obtained commercially.

From the above, it is clear that the compound 1,4,8,11-tetraazacyclotetradecane (aka. cyclam) is a valuable starting material in the preparation of a number of pharmacologically active compounds, including the highly potent anti-HIV compound 1,1'-[1,4-phenylenebis(methylene)]-bis-1,4,8,11-tetraazacyclotetradecane. However, since cyclam is expensive and not readily available, there was a need to develop a more practical process for preparing 1,4,8,11-tetraazacyclotetradecane.

SUMMARY OF THE INVENTION

The present invention relates to a more simple and environmentally acceptable process for preparing 1,4,8,11-tetraazacyclotetradecane employing two inexpensive and readily available starting materials, viz., 1,3-diaminopropane and chloroacetyl chloride. More particularly, the present invention involves the bisacylation of an acyclic diamine to obtain a dichlorodiamide compound in a first step, the cyclization of said diamide compound to obtain dioxocyclam in a second step, and the reduction of dioxocyclam in a third step to obtain the desired 1,4,8,11-tetraazacyclotetradecane.

DETAILED DESCRIPTION OF THE INVENTION

The present invention relates to an improved process for preparing 1,4,8,11-tetraazacyclotetradecane. More particularly, said compound is prepared by a three-step process ad depicted below:

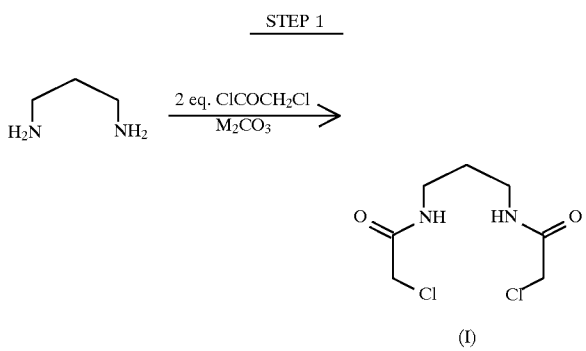

where M is an alkali metal.

-continued
STEP 2

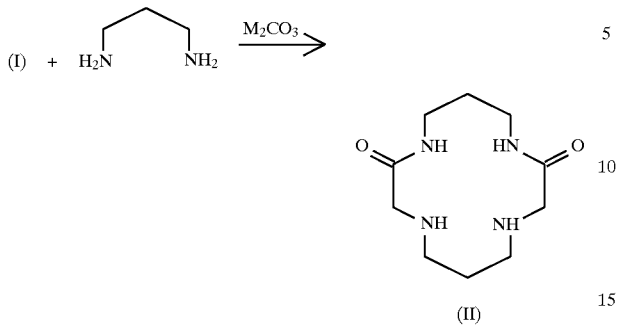

where M is as defined above.

STEP 3

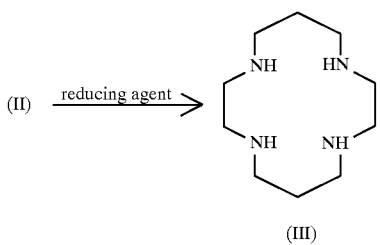

With respect to the individual steps, Step 1 involves the bisacylation of 1,3-diaminopropane with 2 equivalents of chloroacetyl chloride in the presence of an alkali metal carbonate such as potassium carbonate to yield the dichlorodiamide compound of formula I. The bisacylation reaction is carried out in the presence of water and a chlorinated aliphatic hydrocarbon such as methylene chloride at a temperature of from 0° to 30° C. for a period of between 90 minutes and 4 hours.

Step 2 concerns the cyclization of the compound prepared in Step 1, i.e., the dichlorodiamide compound of formula I, by reacting it with an equivalent amount of 1,3-diaminopropane in the presence of an alkali metal carbonate such as sodium carbonate to obtain dioxocyclam of formula II. The cyclization is carried out in the presence of acetonitrile at a temperature of from 78° to 83° C. for a period of between 20 and 30 hours.

Step 3 involves the reduction of the compound prepared in Step 2, i.e., dioxocyclam of formula II, by reacting it with a reducing agent such as Red-A1® (sodium bis (2-methoxyethoxy)aluminum hydride), lithium aluminum hydride or borane-THF complex to obtain the desired compound of formula III. The reduction is carried out in the presence of an aromatic hydrocarbon such as toluene at a temperature of from 20° to 35° C. for a period of between 90 minutes and 4 hours.

As alluded to above, the diamine compound and the chloroacetyl chloride employed as the starting materials in Step 1 are known and commercially available.

Although the product of each reaction described above may, if desired, be purified by conventional techniques such as recrystallization (if a solid), the crude product of one reaction may be employed in the following reaction without purification.

The following example is for purposes of illustration only and is not intended to limit in any way the scope of the instant invention.

EXAMPLE a) Preparation of the dichlorodiamide compound of formula I

In a 500 ml., 3-necked, round-bottom flask, equipped with a magnetic stirrer, cooling bath, internal thermometer and additional funnel is dissolved 10.02 g (0.135 mol) of 1,3-diaminopropane in 100 ml of methylene chloride. To the stirred solution is added 80 ml of distilled water and 37.3 g (0.270 mol) of potassium carbonate. The resultant mixture is then cooled to between 0° and 2° C. and to the cooled mixture is added 21.5 ml (0.270 mol) of chloroacetyl chloride, over a period of 60–90 minutes, while the temperature is maintained below 10° C. The reaction mixture is then allowed to warm to room temperature and the resultant suspension is filtered to provide the crude product as a white solid. The crude product is then added to 150 ml of water, stirred vigorously for 2 hours and re-filtered. The precipitate is then dried in a vacuum oven at 60° C. overnight to yield the desired compound as a white solid.

b) Preparation of dioxoacyclam of formula II

To a 2-L, 4-necked, round-bottom flask, equipped with a mechanical stirrer, heating mantle, temperature probe, addition funnel and reflux condenser is added 5.0 g (22.0 mmol) of the dichlorodiamide compound prepared in a) above, 62.5 g (0.500 mol) of sodium carbonate, 1.63 g (22.0 mmol) of 1,3-diaminopropane and 1.5 L of acetonitrile. The resultant suspension is heated to reflux, maintained at reflux temperature for 24 hours, and then allowed to cool to room temperature. The reaction mixture is then filtered and the filtrate is concentrated to provide the crude product as a white solid. The crude product is then chromatographed on 300 ml of silica gel, employing 20–50% methanol in dichloromethane containing ammonium hydroxide (5 drops/100 ml) as the drops/100 ml) as the eluant. The product-containing fractions are then evaporated to yield the desired compound.

c) Preparation of 1,4,8,11-tetraazacyclotetradecane

To a 100 ml, one-necked, round-bottom flask, equipped with a mechanical stirrer, cooling bath, internal thermometer and addition funnel, and which has been purged with nitrogen, is added 10 ml of dry toluene and 5 ml of Red-A1® (65% solution in toluene). The flask is then cooled to 0° C. and 2.41 g (10.6 mmol) of the dioxocyclam prepared in b) above is added, portionwise. The reaction mixture is then allowed to warm to room temperature and stirred overnight, after which time it is cooled to 0° C. and quenched, very carefully, with 10 ml of 1N sodium hydroxide. The organic layer is then dried over anhydrous magnesium sulfate and evaporated to yield one crop of the desired compound. The aqueous layer is then extracted with three 20 ml portions of dichloromethane and dried to obtain a second crop of the desired compound.

What is claimed is:

1. A process for preparing 1,4,8,11-tetraazacyclotetradecane comprising the steps of:

1) bisacylating 1,3-diaminopropane by reacting it with 2 equivalents of chloroacetyl chloride to obtain the dichlorodiamide compound of formula I

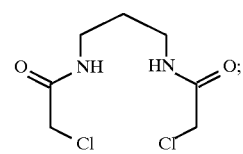

2) cyclizing the dichlorodiamide compound prepared in the first step by reacting it with an equivalent amount of 1,3-diaminopropane to obtain dioxocyclam of formula II

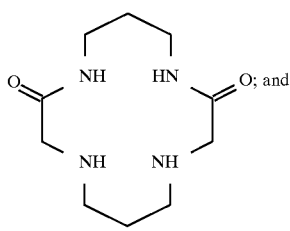

3) reducing the dioxocyclam compound prepared in the second step by reacting it with sodium bis(2-methoxyethoxy) aluminum hydride to obtain 1,4,8,11-tetraazacyclotetradecane of formula III

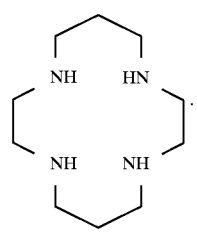

2. A process according to claim 1 wherein the bisacylation reaction is carried out in the presence of an alkali metal carbonate.

3. A process according to claim 2 wherein the alkali metal carbonate is potassium carbonate.

4. A process according to claim 2 wherein the reaction is carried out in the presence of a chlorinated aliphatic hydrocarbon at a temperature of from 0° to 30° C. for a period of between 90 minutes and 4 hours.

5. A process according to claim 4 wherein the reaction is carried out in the presence of methylene chloride at a temperature of from 0° to 30° C. for a period of between 90 minutes and 4 hours.

6. A process according to claim 1 wherein the cyclization reaction is carried out in the presence of an alkali metal carbonate.

7. A process according to claim 6 wherein the alkali metal carbonate is sodium carbonate.

8. A process according to claim 6 wherein the reaction is carried out in the presence of acetonitrile at a temperature of from 78° to 83° C. for a period of between 20 and 30 hours.

9. A process according to claim 1 wherein the reduction is carried out in the presence of an aromatic hydrocarbon at a temperature of from 20° to 35° C. for a period of between 90 mintues and 4 hours.

10. A process according to claim 9 wherein the reduction is carried out in the presence of toluene at a temperature of from 20° to 35° C. for a period of between 90 minutes and 4 hours.

11. A process for preparing 1,4,8,11-tetraazacyclotetradecane comprising the steps of:

1) bisacylating 1,3-diaminopropane by reacting it with 2 equivalents of chloroacetyl chloride in the presence of an alkali metal carbonate and a chlorinated aliphatic hydrocarbon at a temperature of from 0° to 30° C. for a period of between 90 minutes and 4 hours to obtain the dichlorodiamide compound of formula I

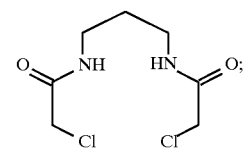

2) cyclizing the dichlorodiamide compound prepared in the first step by reacting it with an quivalent amount of 1,3-diaminopropane in the presence of an alkali metal carbonate and acetonitrile at a temperature of from 78° to 83° C. for a period of between 20 and 30 hours to obtain dioxocyclam of formula II

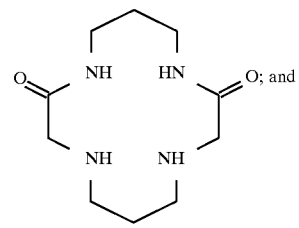

3) reducing the dioxocyclam compound prepared in the second step by reacting it with sodium bis(2-methoxyethoxy) aluminum hydride in the presence of an aromatic hydrocarbon at a temperature of from 20° to 35° C. for a period of between 90 minutes and 4 hours to obtain 1,4,8,11-tetraazacyclotetradecane of formula III

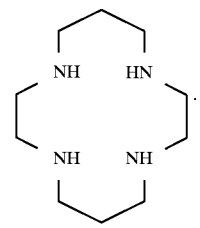

* * * * *